United States Patent [19]

Monson

[11] Patent Number: 4,946,453

[45] Date of Patent: Aug. 7, 1990

[54] WEIGHT REDUCING ATHLETIC GARMENT

[76] Inventor: Demetrius A. Monson, 567 San Nicolas, Third Floor, Newport Beach, Calif. 92660

[21] Appl. No.: 181,683

[22] Filed: Apr. 14, 1988

[51] Int. Cl.[5] .................... A61F 7/00

[52] U.S. Cl. .................... 604/312; 2/2.1 R; 128/379

[58] Field of Search .................... 604/312; 2/2.1 R, 79; 128/379-382, 384

[56] References Cited

U.S. PATENT DOCUMENTS

| | | | |
|---|---|---|---|
| 824,456 | 6/1906 | Walter | 450/97 |
| 854,763 | 5/1907 | Soriven . | |
| 1,249,446 | 12/1917 | Mell . | |
| 1,277,074 | 8/1918 | Hitzeman . | |
| 1,329,025 | 1/1920 | Smith . | |
| 1,638,592 | 8/1927 | Monheimer . | |
| 1,657,094 | 1/1928 | Rutledge . | |
| 1,897,619 | 10/1931 | Powell . | |
| 2,352,128 | 3/1942 | Shikles, Jr. . | |
| 2,664,570 | 9/1950 | Artzt . | |
| 3,028,857 | 4/1962 | Parker | 128/24.1 |
| 3,086,214 | 4/1963 | Lash . | |
| 3,092,110 | 6/1963 | Duensing | 604/312 |
| 3,175,560 | 3/1965 | Menzies | 604/312 |
| 3,310,052 | 3/1967 | Ward | 604/312 |
| 3,529,601 | 9/1970 | Kirkland | 604/312 |
| 3,744,053 | 7/1973 | Parker et al. | 2/2.1 R |
| 3,771,169 | 11/1973 | Edmund | 2/2.1 R |
| 4,276,341 | 6/1981 | Tanaka | 428/246 |
| 4,293,957 | 10/1981 | Melarvie | 2/2.1 R |
| 4,494,246 | 1/1985 | Tillbrook | 2/2.1 R |
| 4,625,336 | 12/1986 | Derderian | 2/79 |
| 4,710,978 | 12/1987 | Pankopf | 2/2.1 R |
| 4,722,099 | 2/1988 | Kratz | 2/79 |

FOREIGN PATENT DOCUMENTS

| | | | |
|---|---|---|---|
| 702435 | 1/1965 | Canada . | |
| 2059046 | 8/1971 | Fed. Rep. of Germany . | |
| 2227411 | 1/1973 | Fed. Rep. of Germany . | |
| 2626765 | 12/1977 | Fed. Rep. of Germany . | |
| 979205 | 4/1951 | France | 2/2.1 R |
| 1357782 | 2/1963 | France . | |
| 2256729 | 1/1974 | France . | |
| 2309164 | 1/1975 | France . | |
| 2344239 | 3/1975 | France . | |
| 2498059 | 1/1981 | France . | |
| 440164 | 12/1935 | United Kingdom . | |
| 1266927 | 3/1972 | United Kingdom . | |

*Primary Examiner*—Stephen C. Pellegrino
*Assistant Examiner*—Mark O. Polutta
*Attorney, Agent, or Firm*—Knobbe, Martens, Olsen & Bear

[57] ABSTRACT

A weight reducing athletic garment, effective at focusing weight loss on specific, predetermined body areas is fabricated from a combination of a nonporous insulative material and a stretch fabric. The nonporous nature of the insulative material causes an increase in prespiration to those areas of the wearer's body which are covered by the insulative segments. The elastic fabric segments have a substantial ability to transmit perspiration, and thereby allow ventilation to other body parts so as to minimize the risk of dehydration. Additionally, elastic segments are disposed near all joint areas to allow the wearer to enjoy more freedom of movement during exercise.

18 Claims, 2 Drawing Sheets

WEIGHT REDUCING ATHLETIC GARMENT

BACKGROUND OF THE INVENTION present invention relates generally to the field garments, and more particularly to an athletic garment, made with at least two types of material having different insulative qualities, and which are designed to cover specific body parts.

Despite a regular and vigorous schedule of exercise, many individuals find that it is difficult to reduce flabbiness on specific body parts, such as the waistline or calves. Various garments have been designed for use during exercise to increase perspiration and cause weight reduction, but none have been effective at "spot reduction," or the focusing of weight loss on specific, predetermined body parts.

One example of a weight reducing garment is a loose fitting "rubber suit" formed entirely from a thin layer of non porous rubberized material. Elasticized cuffs and waistbands on the garment prevent ventilation to the wearer, thus encouraging perspiration.

It has also been found common among body builders to wear "wet suits," designed for water sports, during their workouts so as to increase perspiration throughout the body, thus reducing excess weight and increasing muscular definition. Conventional wet suits are typically made of a relatively heavy nonporous neoprene rubber material, which clings very closely to the body of the wearer. Considerable effort is required to move one's arms and legs when wearing the wet suit, thus restricting freedom of movement during exercise. Further, because of the tight fit and the relative inelasticity of the heavy rubber material from which they are made, wet suits are somewhat difficult to put on and take off.

A drawback common to the use of wet suits and rubber suits for slimming purposes is that since the suits cover a substantial portion of the body without providing ventilation, dehydration and other health risks may be imposed during strenuous workouts.

Waist belts, also made of neoprene, have also been used to facilitate increased perspiration around the waistline and abdominal area to effect slimming. While this type of belt focuses its effects on the waist, it does not facilitate slimming in other areas of the body. Areas such as the thighs, buttocks and triceps are prone to the accumulation of excess body fat, and also require attention. Further, waist belts of this nature have a tendency to curl, or become wadded, thus decreasing the surface area which it covers and, ultimately, the area to be slimmed.

There have been several garments heretofore made which have used a multiplicity of materials to provide different levels of insulation to various body parts. An example of such a garment is disclosed in U.S. Pat. No. 4,625,336, which describes a garment which includes first panels, made of a relatively open mesh fabric which covers the large, hard-working muscles of the wearer, and second panels, made of a tightly knit fabric which covers the tendons and fragile muscles of the wearer. The purpose of this garment is to allow ventilation of the large, hard-working muscles during exercise, and at the same time maintain warmth in the smaller muscles and fragile tendons. However, none of these multifabric garments has been suitable for use in slimming specific body parts.

Accordingly, there is a need in the art for an entire garment which facilitates increased perspiration to specific areas and provides a tight fit so as to have an attractive appearance and maintain complete coverage of desired body parts without unduly restricting the movement of the wearer.

SUMMARY OF THE INVENTION

Briefly, the invention is a warm-up suit which is fabricated from a combination of an insulative material, such as neoprene, and a stretch fabric which allows ventilation, such as lycra. The neoprene and lycra are joined together so as to form a tight fitting garment, such as a body suit, warm up pants, etc. To provide a more stylish-looking garment, the neoprene segments may be covered with lycra material, so as to make the neoprene segments substantially undetectable.

The neoprene is a closed cell rubber structure which is chosen so as to prevent ventilation of the area which it covers, thereby increasing body warmth and resulting in perspiration and slimming by virtue of excess water loss due to the increased perspiration. Lycra is a woven stretch fabric which is comfortable, stylish, form fitting and permits ventilation.

The neoprene portions of the garment are positioned and sized to cover specific body parts, such as the stomach, buttocks, and thighs, on which the wearer wishes to effect slimming. Unlike a full neoprene garment, the garment of the present invention allows ventilation through the lycra portions, and provides added flexibility and ventilation in areas of the body where weight reduction is not critical. Advantageously, the lycra portions are positioned to cover the wearers joints, thus minimizing the resistance to movement imposed by the garment.

To facilitate the ease with which the garment may be put on and taken off, lycra segments are disposed throughout the garment so that the neoprene material does not completely encircle any body part, such as the torso, arms or legs. The lycra extends between the neoprene portions to increase the elasticity of the garment.

The combination of neoprene and lycra can be used for a variety of garments ranging from shorts to pants to full body suits. The specific pattern of neoprene and lycra can be varied on a customized basis for each wearer so as to focus on the body parts which that wearer seeks to reduce.

Alternatively, the garment can be formed entirely of a single type of elastic fabric which permits ventilation. Those portions of the garment which cover body parts on which weight loss is desired can then be coated with a rubber material to render those portions non-porous.

DETAILED DESCRIPTION OF THE PREFERRED EMBODIMENT

Figure 1:
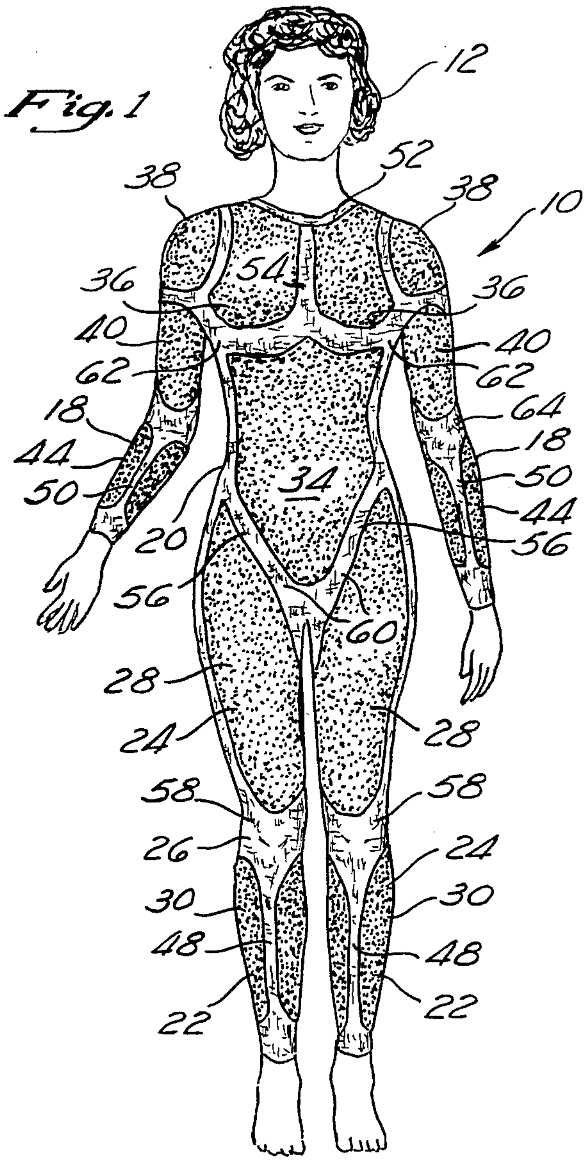
FIG. 1 is a frontal view of a preferred embodiment of the garment of the present invention, schematically depicted as being worn by a wearer.
Figure 2:
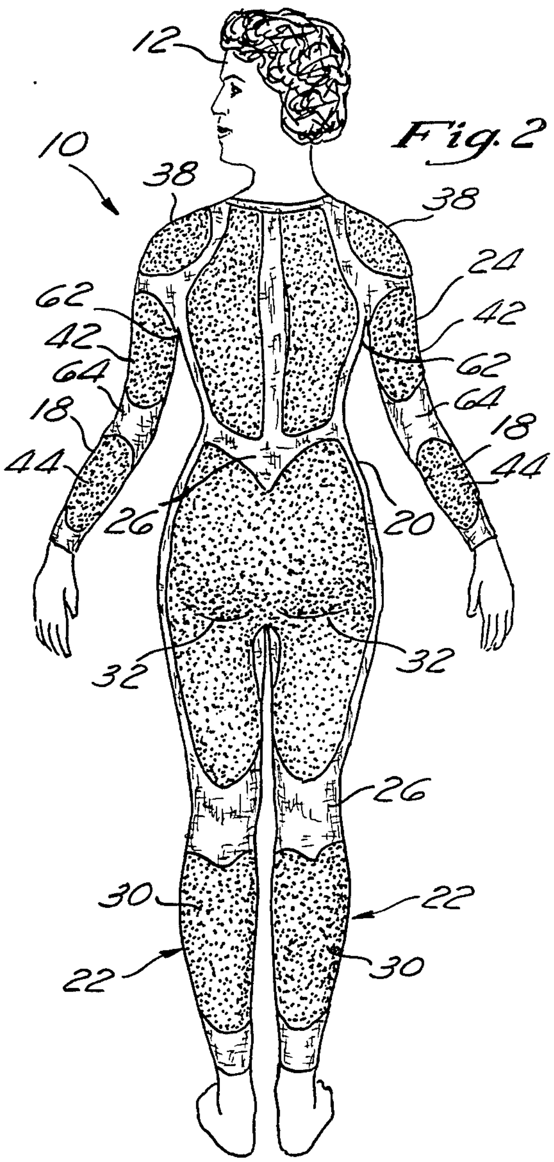
FIG. 2 is a rear view of the garment in FIG. 1.

In accordance with one aspect of the present invention, and with reference to FIGS. 1 and 2, there is depicted a form-fitting athletic garment 10, as worn by a wearer 12, having a front side, shown in FIG. 1, and a back side, shown in FIG. 2. The garment is adapted to fit the wearer's body, as a full body suit, and exhibits arm portions 18, a trunk portion 20, and leg portions 22. As schematically depicted in the drawings, the garment 10 is comprised of two types of materials, represented by shaded and unshaded areas, 24 and 26, respectively.

For many individuals, despite a vigorous workout program, it remains difficult to reduce flabbiness in certain body parts. Areas such as the thighs 28, calves 30, buttocks 32 and abdominal area 34, are representative of such bodily regions. Additionally, for most body builders increased muscular definition in the upper chest area 36, shoulders 38, biceps 40, triceps 42 and forearms 44 is of paramount importance. Accordingly, the garment 10 of the present invention selectively provides segments 24 of non-porous, insulative material to these areas. The insulative portions 24 of the garment 10 are adapted to prevent ventilation to those areas of the body which they cover. By preventing ventilation to these body parts, the wearer 12 of the garment 10 is caused to perspire more profusely, thereby facilitating reduction of excess weight on specific body parts as desired.

The shaded areas are representative of those segments 24 of the garment which are made from such an insulative material. These insulative segments are adapted to cover those areas of the wearer's body where fatty tissue is most concentrated, or where spot reduction is most desired. Preferably, the insulative segments 24 are made of a nonporous, closed cell material which is elastic. Particularly suitable for this purpose is neoprene rubber, a material commonly used in the making of wet suits. Alternatively, in place of neoprene, a rubberized fabric may be used.

To allow ventilation, increase flexibility of the garment and to facilitate the ease with which the garment may be put on and taken off, elastic fabric segments 26 are disposed throughout the garment 10. These fabric segments 26 have a much higher elasticity than that of the insulative segments 24, and stretch to closely conform the wearer's anatomy. Further, the elastic fabric is preferably woven, so as to allow ventilation to the wearer's body and minimize the risk of dehydration or other risks which may be imposed during a strenuous workout.

As depicted by the unshaded areas of FIGS. 1 and 2, elastic fabric segments 26 are disposed along the sides of the thighs 46, shins 48, inner forearm 50, clavicle 52, sternum 54 and pelvic area 56, so as not to allow the insulative material 24 to completely encircle any body part. Elastic segments 26 are also provided to cover joints and other areas of excessive movement, such as the knees 58, groin 60, armpits 62 and elbows 64. The latter of these elastic fabric segments yield readily to the necessary body movements of the wearer during exercise.

The elastic fabric segments 26 may be formed from any woven or knitted fabric which has a greater elasticity, resilience and stretchability than that of the insulative material 24. Particularly suitable for the elastic fabric is Lycra.

The elastic fabric segments 26 and the insulative material segments 24 are joined together, along their adjacent peripheries by sewing, to form a tight-fitting garment 10 which readily conforms to the contours of the wearer's body. More preferably, the garment 10 of the present invention is sewn together by elastic seams, which further enhance the ease with which the garment may be adorned and removed.

In use, the elastic fabric segments have a substantial ability to transmit perspiration from the body of the wearer, while the insulative segments are adapted to increase body warmth by preventing such ventilation. This increased body warmth facilitates increased perspiration throughout the areas covered by the insulative material and thereby effects slimming.

Figure 3:
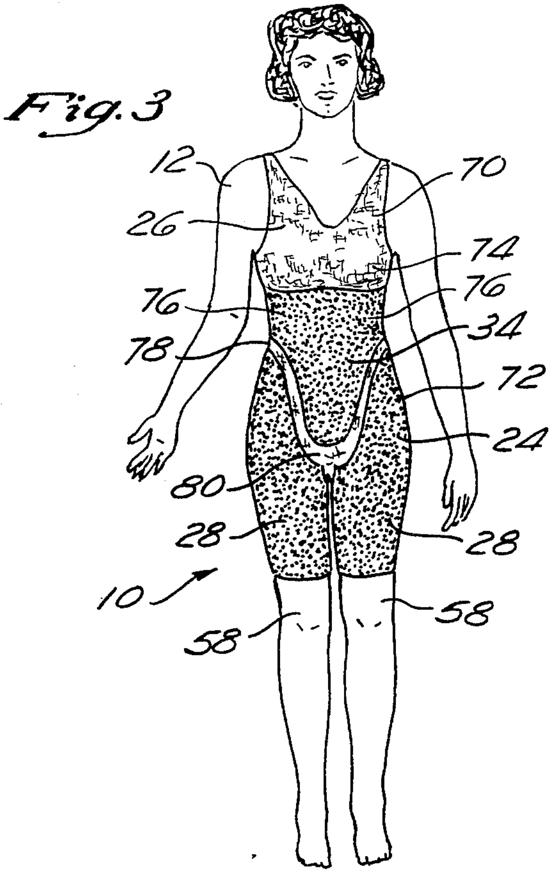
FIG. 3 is a frontal view of an alternative embodiment of the garment of the present invention.
Figure 4:
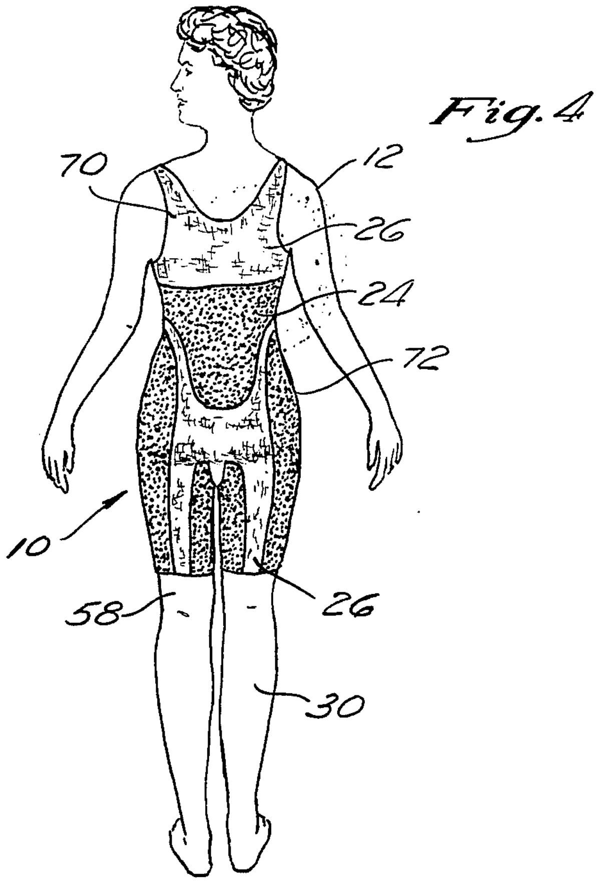
FIG. 4 is a rear view of the garment depicted in FIG. 3.

In accordance with another aspect of the present invention, and with reference to FIGS. 3 and 4, there is provided a modified athletic garment, exhibiting a sleeveless upper portion 70, connected to a shorts-like portion 72, which extends to just above the knee 58 of the wearer 12. In this embodiment, insulative material is disposed below the mammary region 74, and extends toward the abdominal area 34. A portion 76 of the insulative material, directly under the mammary region 74 but above the waist 78, encircles the trunk of the wearer. Large insulative segments are also provided to cover the thighs 28. An elastic fabric segment is disposed around the crotch area 80 on the front side, shown in FIG. 3, of the garment 10, and extends upwardly toward the waist 78 and around the pelvis. The elastic segment continues around the back side, shown in FIG. 4, of the garment 10, in a H-shape manner, so as to facilitate the necessary movements of the wearer during a workout.

In either embodiment, the insulative material segments may be concealed by covering them with the elastic fabric, so as to enhance the aesthetic qualities of the garment. For example, an outer layer of lycra fabric may be bonded to the neoprene portions.

In an alternative embodiment, the entire garment may be formed of a single type of elastic fabric having several segments (not shown) sewn together along seams in the conventional fashion for that particular type of garment. The insulative segments 24 in such an embodiment would be formed by coating desired areas of the garment 10 with a layer of natural or artificial rubber, or rubber-like material. The coating may be applied to the garment as an aqueous latex material and then allowed to cure. Once the latex has cured, insulative segments 24 will be formed by the specific areas to which the latex was applied. The remaining, uncoated portions of the garment will form the elastic segments 26 of the garment 10. In contrast, in the previously described embodiment, the insulative and elastic segments are discreet and are joined together by a separate assembly process, such as by sewing. Also, unlike the previous embodiment, the peripheries of the insulative and elastic segments do not need to correspond to the seams of the garment.

Although certain specific embodiments of the invention have been shown and described, it should be readily apparent that many modifications are possible. The invention is therefore not intended to be restricted to the exact showing of the drawings and description thereof, but is considered to include reasonable and obvious equivalents.

I claim:

1. A form-fitting athletic garment, adapted to effect slimming to certain specified areas of the body, said garment comprising a full body suit, adapted to substantially cover a wearer's upper and lower torso below the wearer's neck, both arms above the wearer's wrists, and both legs above the wearer's ankles, said body suit comprised of:

at least one first segment, adapted to cover first areas of the body where fatty tissue is concentrated, said first segment formed from an insulating material so as to prevent ventilation to said first areas and facilitate increased perspiration to effect slimming;

at least one second segment of homogeneous material, adapted to exclusively cover second areas of the body by conforming to and directly engaging said second areas so as to minimize the insulation provided to said second areas, said second segment formed from porous elastic fabric so as to allow ventilation to said second areas, and adapted to facilitate freedom of movement; said second segment constructed only in single layer applications; and said first and second segments arranged discretely; whereby said first and second segments are joined together to form said garment which is worn while exercising.

2. A form-fitting athletic garment, as defined by claim 1, wherein said insulating material is a rubberized material.

3. A form-fitting athletic garment, as defined by claim 1, wherein said elastic fabric is lycra.

4. The garment of claim 1 wherein the periphery of said first segment abuts the periphery of said second segment.

5. A form-fitting athletic garment, as defined in claim 1, wherein said first segment covers exclusively only the entire abdomen, buttocks and hip area, while the second segment covers the remaining muscles enclosed within the garment.

6. A form-fitting athletic garment as defined by claim 1, wherein said insulating material is less elastic than said elastic fabric.

7. A form-fitting athletic garment as defined by claim 6, wherein said first segment does not completely encircle any body part so as to facilitate adornment and removal of said garment.

8. A form-fitting athletic garment, as defined by claim 1, wherein said insulating material is a closed cell material.

9. A form-fitting athletic garment, as defined by claim 8, wherein said insulating material is neoprene rubber.

10. A form-fitting athletic garment, as defined by claim 1, wherein said first area of the body, which is covered exclusively by said first segment, includes portions of the leg, arms, buttocks and abdominal area.

11. A form-fitting athletic garment, as defined by claim 10, wherein said second area of the body which is exclusively covered by said second segment includes muscle groups on which the wearer is not desirous of losing weight as well as the joints and bony areas.

12. A form-fitting athletic garment which, when adorned by a wearer, is adapted to facilitate increased perspiration where fatty tissue readily accumulates, said garment also adapted to permit increased flexibility and to allow ventilation to the body where fatty tissue is not prone to accumulate, said garment comprising:

at least one first segment adapted to exclusively cover certain first areas of the body, including portions of the legs, buttocks, and abdominal area, said first segment formed of an insulating elastic material so as to substantially prevent ventilation to said first areas;

at least one second segment of homogeneous material, adapted to exclusively cover certain second areas of the body, including muscles not included in said first areas as well as joints and bony areas, by conforming to and directly engaging said second areas so as to minimize the insulation provided to said second areas, said second segment formed from a single layer of porous elastic fabric so as to allow ventilation to said second areas and to facilitate the wearer's agility when wearing the garment; and said first and second segments arranged discretely, whereby said individual segments are joined together so as to form said form-fitting garment.

13. A method for producing a form fitting athletic garment which is designed to effect slimming on preselected body parts of a wearer on which fat deposits tend to accumulate, said method comprising the steps of:

fabricating a form fitting athletic garment from an elastic, porour material which permits flexibility of the wearer while also providing ventilation to the wearer; and coating portions of said garment with a rubber material so as to effect a single-layer of composite material which is substantially nonporous, thus forming insulative portions of said garment, said insulative portions covering body parts of the wearer on which slimming is desired, the remainder of said garment not coated with rubber material forming porour elastic portions of said garment which permit ventilation to muscles areas where fat accumulation is low and which cover joints of the wearer so as to permit flexibility.

14. A form fitting athletic garment, adapted to effect slimming to certain specified areas of the body, said garment comprising:

a plurality of first segments, adapted to cover first areas of the body where fatty tissue is concentrated and weight loss is desired, said first segments including first and second pectoral panel each covering the pectoral muscle, a first and second shoulder panel each covering the shoulder joint; a first and second forearm panel each covering a portion of the forearm, a first and second biceps panel each covering a portion of the upper arm, an abdomen panel covering the abdomen from the sternum area to the groin area and extending to each side of the body, a first and second back panel covering the left and right side of the back respectively and each extending from the neck down to the lower back region and from the side of the body to the spine area, a hind panel covering the buttocks and extending down across the back of each thigh, a first and second thigh panel each covering the front of the thigh extending from the hip area to knee area, a first and second calf panel each encircling a portion of the calf, said first segments formed from an insulating material;

a plurality of second segments, adapted to cover second areas of the body where ventilation is desired, said second segments including first and second forearm panels each encircling the wrist and running longitudinally along the forearm up to and around the elbow, a first and second shoulder panel each encircling the top of the arm below the shoulder joint and running from the front of the armpit up and over the shoulder blade and back down to the back under-arm, a chest panel running across the chest and stretching from said first shoulder panel to said second shoulder panel, a sternum panel running from the middle of said chest panel up to and around the neck, a first and second knee panel each encircling the knee and running along the shin down to and around the top of the foot, a first and second side panel each running from the corresponding shoulder panel at the armpit down along the side of the body to the corresponding knee panel, a lower back panel running across the lower back directly above the buttocks stretching from said first side panel to said second side panel, a spine panel running from the middle of said lower back panel along the spine to the said sternum panel at the nape of the neck, a groin panel covering the groin area and a portion of the top of each inner thigh, a lower abdomen panel running from said first side panel at the hip area down along the top of the leg to said groin panel and continuing up to said second side panel at the hip area,

15. A form fitting athletic garment, adapted to effect slimming to certain specified areas of the body, said garment a plurality of first segments, adapted to cover first areas of the body where fatty tissue is concentrated and weight loss is desired, said first segments including an upper panel covering the abdomen from the stomach region down to the groin in the front and also covering the lower back region, a first and second lower panel each covering the hip area and a portion of the thigh down to the knee area, said first segments formed from an insulating material;

a plurality of second segments, adapted to cover second areas of the body where ventilation is desired, said second segments including a hind panel covering a portion of the buttocks and extending down the back of each thigh, a groin panel covering the groin area, a hip panel extending from the upper right portion of said hind panel around the right hip down to said groin panel up to and around the left hip and down to the upper left portion of said hind panel, said second segments separating all first segments, said second segments made of an elastic open-mesh fabric.

16. A form-fitting partial body suit, adapted to substantially cover the upper and lower torso of a wearer, as well as the wearer's thighs, said body suit further adapted to effect slimming to certain specified areas of the body covered, said body suit comprising:

at least one first segment, adapted to cover first areas of the body where fatty tissue is concentrated, said first segment formed from an insulating material so as to prevent ventilation to said first areas and facilitate increased perspiration to effect slimming;

at least one second segment of homogeneous material, adapted to exclusively cover second areas of the body by conforming to and directly engaging said second areas so as to minimize the insulation provided to said second areas, said second segment formed from porous elastic fabric so as to allow ventilation to said second areas, and to facilitate freedom of movement; said second segment constructed only in single layer applications; and said first and second segments arranged discretely; whereby said first and second segments are joined together to form said garment which is worn while exercising.

17. A form-fitting full pants suits, adapted to cover the lower torso of a wearer below the wearer's waistline, and substantially the entire legs of the wearer, said full pants suit further adapted to effect slimming to certain specified areas of the body covered, said full pants suit comprising:

at least one first segment, adapted to cover first areas of the body where fatty tissue is concentrated, said first segment formed from an insulating material so as to prevent ventilation to said first areas and facilitate increased perspiration to effect slimming;

at least one second segment of homogeneous material, adapted to exclusively cover second areas of the body by conforming to and directly engaging said second areas so as to minimize the insulation provided to said second areas, said second segment formed from porous elastic fabric so as to allow ventilation to said second areas, and to facilitate freedom of movement; said second segment constructed only in single layer applications; and said first and second segments arranged discretely; whereby said first and second segments are joined together to form said garment which is worn while exercising.

18. A form-fitting short pants suit, adapted to cover the thighs of the wearer and the lower torso of the wearer below the waistline, said short pants suit further adapted to effect slimming to certain specified areas of the body covered, said short pants suit comprising:

at least one first segment, adapted to cover first areas of the body where fatty tissue is concentrated, said first segment formed from an insulating material so as to prevent ventilation to said first areas and facilitate increased perspiration to effect slimming;

at least one second segment of homogeneous material, adapted to exclusively cover second areas of the body by conforming to and directly engaging said second areas so as to minimize the insulation provided to said second areas, said second segment formed from porous elastic fabric so as to allow ventilation to said second areas, and to facilitate freedom of movement; said second segment constructed only in single layer applications; and said first and second segments arranged discretely; whereby said first and second segments are joined together to form said garment which is worn while exercising.

* * * * *